United States Patent [19]

Kawai et al.

[11] Patent Number: 4,772,390
[45] Date of Patent: Sep. 20, 1988

[54] WATER PURIFYING METHOD AND SYSTEM

[75] Inventors: Atsushi Kawai, Nagoya; Ikuo Igami, Toyoake; Yuzuru Katagiri, Nagoya; Michio Inoue, Kasugai; Hisao Tanaka, Nagoya, all of Japan

[73] Assignee: Mitsubishi Rayon Co., Ltd., Tokyo, Japan

[21] Appl. No.: 786,718

[22] Filed: Oct. 15, 1985

Related U.S. Application Data

[63] Continuation of Ser. No. 427,618, Sep. 29, 1982, abandoned.

[30] Foreign Application Priority Data

Jan. 25, 1982 [JP] Japan .................................. 57-9894
Mar. 23, 1982 [JP] Japan ................................. 57-45983

[51] Int. Cl.⁴ .............................................. B01D 13/01
[52] U.S. Cl. ........................... 210/321.78; 210/323.2; 210/335; 210/433.2; 210/436; 210/472
[58] Field of Search ................. 210/321.1, 323.2, 335, 210/433.2, 436, 472; 427/618

[56] References Cited

U.S. PATENT DOCUMENTS 3,503,515  3/1970  Tomsic .............................. 210/321.1
4,265,762  5/1981  Brenholt ........................... 210/436 X
4,401,567  8/1983  Shindo et al. ...................... 210/500.2

FOREIGN PATENT DOCUMENTS 2440217  5/1980  France ............................. 210/321.1

OTHER PUBLICATIONS

Millipore Bulletin MB410, *A Primer on Microfiltration Technology*, Millipore Corp. Bedford, Mass., 2/1972, pp. 1–16.

Primary Examiner—Frank Sever
Attorney, Agent, or Firm—Oblon, Fisher, Spivak, McClelland & Maier

[57] ABSTRACT

Water contaminated by small amounts of bacteria, pyrogens and low molecular weight organic compounds is treated by passing said contaminated water through a microporous polyolefin membrane having a multitude of rectangularly shaped nodule areas, each nodule area containing a plurality of strip-like microfibrils arranged in a longitudinal direction from one surface of a nodule to the side opposite said surface thereby forming a plurality of strip-like micropores in each nodule, said micropores being contiguous with each other from one surface to the other surface of the membrane thereby forming a micro-stacked structure, the mean pore diameter of said micropores ranging from 0.03 to 0.8 μ.

2 Claims, No Drawings

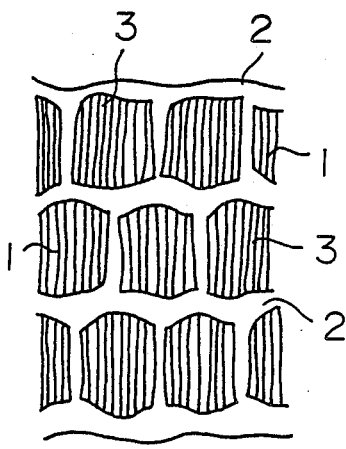

WATER PURIFYING METHOD AND SYSTEM

This application is a continuation of application Ser. No. 427,618, filed Sept. 29, 1982 now abandoned.

BACKGROUND OF THE INVENTION

1. Field of the Invention

The present invention relates to a method of purifying water and to a water purification system. More particularly, the invention relates to a method and system for the purification of water for a variety of applications including the preparation of drugs, as drinking water, and for use in administering medical care and in the food industry, in the precise electronic industry and for physical and chemical experiments.

2. Description of the Prior Art

In a variety of applications such as those described above, it is essential that water be available which is free of such materials as colloidal substances, bacteria, pyrogens and harmful organic substances. In order to obtain purified water, such conventional methods and systems as distillation, ultrafiltration and reverse osmosis are being used. However, these systems to be most efficient should be employed on a large scale, and the high operating costs of these systems are a serious problem. Further, these methods and systems are frequently inadequate for obtaining clean water in necessary amounts. Moreover, it is essential that the clean water used in the medical care of people should not contain any bacteria and should be free of pyrogens. Pyrogen is a generic name for pyrogenic substances such as the metabolites of bacteria, fungi and yeast, which are defined as substances which induce exothermal reactions in an organism upon injection. Chemically, pyrogens are said to be heat-resistant, high molecular weight complex glycolipids containing nitrogen and phosphorous, and are of a particle size of 1–5 m$\mu$ and are water-soluble. Pyrogens in micro-amounts of about 0.01 $\mu$g/kg are reported to induce pyrogenic reactions in an organism. Pyrogens entering an organism such as by injection into the blood, by infusion-solution, drugs, and the like will cause such side effects as fever or shock. Accordingly, the water which is used for medical care should be germless and pyrogen-free. However, pyrogens cannot be removed from water or be destroyed by the bacteria-filtering method or the high-pressure steam-sterilizing method. Thus, specialized water-treating methods must be used to obtain pyrogen-free water. Moreover, the presence of harmful substances in the low molecular weight organic compounds present in water in small amounts besides bacteria and pyrogen, is further reason for the thorough purification of water. In terms of the present invention, a "small amount" means amounts in the ranges of parts per billion (p.p.b.) and parts per trillion (p.p.t.).

It is particularly desirable to be able to efficiently remove such organic compounds as phthalate esters (dibutyl phthalate, dioctyl phthalate, and the like), straight-chain dibasic acid esters (dioctyl adipate, dioctyl azelate, dioctyl sebacate, and the like), other higher fatty acid esters, higher-fatty acids, and other halogenated benzenes which are present in water in amounts of from several p.p.t. to hundreds p.p.t. As mentioned above, there are many organic compounds which are hardly soluble in water, and are therefore present in minor amounts in water, and yet, such organic compounds are found to be increasing in concentration in river water and underground water year after year around concentrated population centers, in cities and industrial areas. Therefore, a need continues to exist for a very efficient method and system for the removal of the above compounds from water because of the unfavorable circumstances from the hygienic viewpoint of the presence of such organic compounds in tap water and well water.

SUMMARY OF THE INVENTION

Accordingly, one object of the present invention is to provide a method and system by which organic compounds and other contaminants present in water in trace amounts can be efficiently and effectively removed.

Briefly, this object and other objects of the present invention, as hereinafter will become more readily apparent, may be attained in a method of purifying water containing small amounts of contaminating bacteria, pyrogens and low molecular weight organic compounds by passing said contaminated water through a microporous polyolefin membrane having a multitude of rectangularly shaped nodule areas, each nodule area containing a plurality of strip-like microfibrils arranged in a longitudinal direction from one surface of a nodule to the side opposite said surface thereby forming a plurality of strip-like micropores in each nodule, said micropores being contiguous with each other from one surface to the other surface of the membrane thereby forming a micro-stacked structure, the mean pore diameter of said micropores ranging from 0.03 to 0.8$\mu$.

In another embodiment of the invention, water contaminated with contaminating bacterial pyrogens and low molecular weight organic compounds is passed through a multi-stage filtering system comprising a plurality of housings each provided with an inlet for water to be treated and an outlet for treated water and each containing at least one of the microporous polyolefin membranes described above.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

The shape of the porous polyolefin membrane used in the present invention may be either a flat film or a tubular membrane. However, a porous hollow fiber membrane, which is a structure having a larger membrane surface area per unit volume, is a particularly favorable structure. Also, porous hollow fibers having the special microstructure mentioned above can be manufactured by proper control of the processing conditions in the hot stretching step after the cold stretching of highly oriented untreated crystalline hollow fibers obtained by melt-spinning of a polymer, e.g., polypropylene or polyethylene, through a special nozzle for manufacturing the hollow fiber.

Reference is made at this point to the drawings for an explanation of the micro-structure of the separating membrane used in the present invention.

Figure 1:
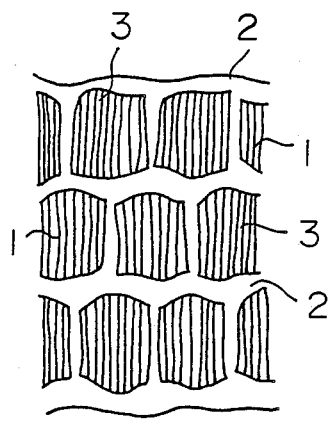
FIG. 1 is a schematic drawing showing the stacking structure of strip-like micropores.

FIG. 1 is a schematic drawing of the stacking structure of strip-like micropores. In FIG. 1, (1) denotes microfibrils, (2) denotes a multitude of rectangularly shaped nodular portions containing the microfibrils (1), while (3) denotes strip-like micropores. The micropores (3), which are composed of microfibrils and nodular portions, form the stacking structure through each nodular portion. The stacking structure of the micropore shows the lamination in the fiber-length direction within one plane through the nodular portion, and simultaneously, it means that the plane having such a structure is piled in the thickness-direction of the wall of the hollow fiber. Such a special micro-structured membrane is a key element in the present process which contributes to the purification of water.

In this invention it is essential that the mean pore diameters of the micropores measured by a mercury porosimeter be $0.03-0.8\mu$. Micropores of a size less than $0.03\mu$ are not favorable from the viewpoint of a marked reduction of water-permeability which results in diminished diameters filtering efficiency. Micropore diameters over $0.8\mu$ are unfavorable because of the reduced trend to efficaciously remove low molecular weight compounds present in water in small amounts as mentioned before, although bacterial removal is possible. The relationship between pore size and membrane material is such that even when the mean pore diameters of the micropore membrane is within the range of $0.03-0.8\mu$, microporous membrane materials other than porous polyolefin membranes are unsatisfactory because of the marked lowering of the rate of removal of the said organic compounds mentioned above. That is, both the microporous structure of the present membrane and the material of the membrane itself which is a polyolefin, are important factors which contribute to the removal of the said organic compound from water by the synergic action of filtering and adsorption.

As for the membrane, its greater water-permeability is an important factor in its practicality and it is desirable that the initial filtering flow rate when filtering distilled water through the membranes should be over 1 liter/min/m$^2$ with a hydraulic pressure of 1 kg/cm$^2$ under normal temperatures. At flow rates less than 1 liter/min/m$^2$ the membrane shows less water-permability with less intake of purifying water per unit hour; thus it is not practical.

The membrane of the present invention has the feature of a micro-stacking structure with strip-like pores, and in spite of the fact that the mean pore diameters of the micropores is as small as $0.03-0.8\mu$, the membrane has a very substantial water-permeability. The efficacy of the membrane becomes much greater by the use of a porous hollow fiber having a porosity of 20-90 vol % as mentioned later. Moreover, the wall thickness of the porous hollow fiber desirably should be $10-100\mu$ for stable industrial production, while a thickness less than $10\mu$ is mechanically weak which presents problems. There is no necessity for the membrane to be over $100\mu$ thick. A thickness of $20-80\mu$ is especially desirable.

The proper range for porosity of the membrane as measured by a mercury porosimeter is 20-90 vol %. The porosity should not be less than 20 vol % because the permeability of water decreases, while the porosity should not be over 90 vol % because the membrane will be weaker mechanically. A rate of 40-80 vol % is especially desirable.

In this invention, no restriction is placed on the diameter of the hollow opening of the porous hollow fiber. Usually, however, a favorable diameter is $200-300\mu$.

In order to be most effective in removing pyrogenic substances from water, it is preferred that the membrane should actually be the microporous polyolefin hollow fiber, the wall thickness T ($\mu$) of the fiber should be $10-100\mu$, the porosity of the membrane as measured by a mercury porosimeter should be 20-90 vol %, the mean pore diameters $\overline{D}$ ($\mu$) of the micropores should be less than $0.03\mu$ and $\overline{D}$ should be less than $0.002 \times T + 0.3$. In the development of the invention, it was not expected that pyrogens, existing in water in small amounts and having a particle size of 1 to 5 m$\mu$, could be removed from water in spite of the fact that the pore diameters of said membrane as measured by a mercury porosimeter is $0.03-0.8\mu$. Moreover, presently, the mechanism of pyrogen removal is not yet clarified. However, pyrogen-removal may be greatly influenced by the piled-up structure of the strip-like micropores composed of nodular portions and microfibrils oriented towards the thickness-direction of the wall of the hollow fiber as shown in FIG. 1. This rationale can be explained, as mentioned later, by the fact that pyrogens are removed even by enlarging the micropore diameters (D) when the wall thickness (T) is enlarged.

On the other hand, as far as pyrogen removal is concerned, a larger pore diameter of the micropores and a larger porosity of the membrane both favor pyrogen removal because of larger permeability of the membrane. As a result of measuring the mean pore diameters of the porous hollow fiber and the porosity of the fiber by a mercury porosimeter, when using the hollow fiber having strip-like micropores mentioned before, the inventors have found that the upper limit of the pore diameters for filtering pyrogens has proved to change by the membrane thickness T ($\mu$) of the hollow fiber membrane. That is, a larger membrane thickness (T) results in no-content of pyrogens in the filtrate even when the membrane possesses a larger mean pore diameters. It seems that a greater membrane thickness does not result in a permeability of the pyrogen through the membrane because the pyrogens are blocked at the microfilbriles of the membrane even when the mean pore diameters is large. In the case of such a porous hollow fiber, the relation between the membrane thickness and maximum pore diameters can be expressed as $\overline{D} = 0.002 \times T + 0.3$, and further, the lower-limit value over $0.03\mu$ has proved to be effective in view of water-permeability. In other words, it has been found that water from which pyrogen has been completely removed can be obtained while maintaining a larger permeation rate by using a hollow fiber having a pore diameter of less than $(0.002 \times T + 0.3)\mu$. Moreover, it is desirable that the membrane thickness of the hollow fiber be $10-100\mu$, with a preferred range being $20-80\mu$. The porosity is 20-90 vol % with a preferred favorable range being 40-80 vol % in view of the balance of physical strength of the membrane and water-permeability.

The water-purifying technique of the present invention in an embodiment in which water is filtered through membranes in a plurality of stages, is satisfactory. The reliability of this embodiment can be improved for the removal of the above-mentioned substances by two or more stages of filtration, and also, by balancing the area and pore diameters of the membranes between the initial and subsequent stages, a far longer service-life can be obtained than can be obtained in a single stage process. In the multi-stage filtering system, $An \geq An+1$, where An is the mean pore diameters of the membrane at the nth stage, A desirable relation is $Sn \geq Sn+1$, where Sn is the surface area of the membrane at the nth stage.

It has been observed in the present process that when low molecular weight organic compounds are present in water in small amounts and when and filtering tap-water, or the like, which contains relatively large amounts of organic compounds, the phenomenon of a quick decrease in the water permeability through the porous membrane as the organic compounds are removed is observed. The multi-stage filtering method of the present invention is especially preferred as a means of preventing the occurrence of the above phenomenon because of the remarkable decrease in water permeability observed, especially in the case of tap water containing over 200 p.p.b. of the organic compounds.

From conventional membrane filtering techniques, it is well known to filter water over 2 filtration stages by the use of membranes having different pore diameters. However, these methods are intended to remove particles from the liquid. On the other hand, the present process is designed to remove dissolved low molecular weight organic compunds and not for particle removal, while minimizing or preventing decreases in water permeability. Accordingly, the mean pore diameters of the film in the initial stage is desirably larger than the mean pore diameters of subsequent stages, and yet, even when the mean pore diameters is the same for the membranes between the initial and subsequent stages, it is possible to prevent water permeability decreases. However, if the mean pore diameters of the membrane in the latter stage is greater than the mean pore diameters of the initial stage, the filtering resistance of the film at the initial stage becomes rate determining and the water permeability is reduced, which result is unfavorable. Also in the present invention, the type of water which is treated is well-water or tap water having relatively few impurities, since it is intended to remove bacteria, pyrogens, and low molecular weight organic compounds all present in small amounts in water by a higher-order treatment. Accordingly, if highly contaminated water is to be treated by the present process, it should be pretreated.

The present invention is intended for the continuous treatment of water immediately before use. Moreover, without using pressurizing means such as pumps, or the like, it is possible to obtain treated water by operating the system with hydraulic pressure alone at the water source by mounting the system of the present invention at the city water tap or at the well-water pipe of the pumping system. For example, such methods as distillation and reverse osmosis can be used as effective means for removing bacteria and pyrogens from water. However, in such cases, the treated water must be stored in a tank for future use, whereby, in many cases, bacteria in the air may enter into the water through pipes or pipe connections. Thus, the treated water becomes contaminated and the water will contain pyrogens as metabolites of bacteria. In order to prevent this situation the present invention has been developed and germfree and pyrogen free water can be obtained with high reliability by the method of the present invention without having to store the treated water just before use.

The water treatment system of the present invention is as follows. The system is a multi-stage filtering system which has more than one housing each having an inlet for water to be treated and an outlet for the discharge of treated water and the disposal of used porous polyolefin membranes. The system is characterized by numerous strip-like micropores formed by microfibrils oriented in the longitudinal direction and nodular portions that are connected to the microfibrils nearly rectangularly. Moreover, the micropores are contiguous with each other in the thickness direction to form a stacked structure with the mean diameters of the micropores ranging from 0.03 to 0.8$\mu$. Accordingly, by this system it is possible to remove bacteria, pyrogens and low molecular weight organic compounds present in small amounts with greater reliability than previously obtainable. Furthermore, the present system is very useful and is able to prevent decreases in water permeability for the above-mentioned reasons by the use of a system provided with a multi-stage filtering mechanism in which $An \geq An+1$, where An is the mean pore diameters of the membrane at the nth stage and $Sn \geq Sn+1$, where Sn is the surface area of the membrane at the nth stage.

Figure 2:
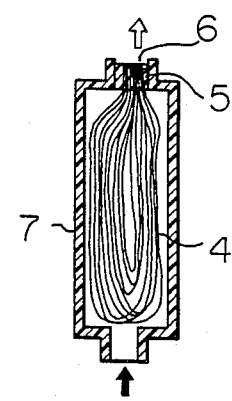
FIGS. 2 and 7 show examples of modules using a hollow fiber.

The present invention is particularly useful in a water-purifying system as shown in FIG. 2 wherein the filtering material is made of a microporous hollow fiber bundle bent into a U shape (4) and bound at the tip with a resin plug (5) while keeping the open ends (6) of the hollow fibers open at the outlet (6) of the housing. The system is provided with a water inlet. The water is treated by permeation through the microporous hollow fiber membrane. In FIG. 2, the water-permeating direction is shown from the outside to the inside of the hollow fiber, but a flow of water in the opposite direction is also satisfactory.

Figure 3:
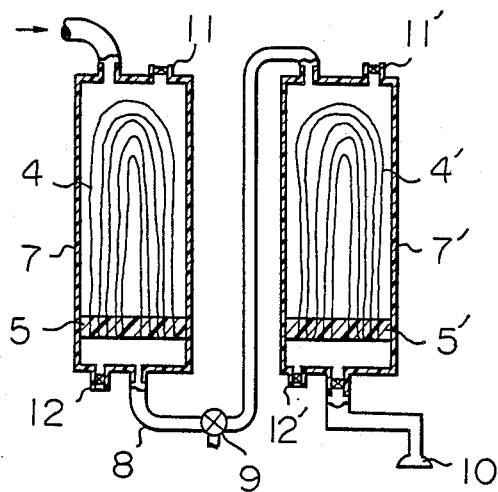
FIGS. 3 and 4 show examples of a multi-stage treating system.

FIG. 3 shows an example of assembled modules in multiple stages, with the system being provided with a shower nozzle (10) which prevents bacterial invasion at the outlet of the treated water. This apparatus is particularly preferable for the preparation of uncontaminated water. The shower nozzle can be made of a plastic material, having adsorbed thereon iodine which is used as a disinfectant. In conventional systems for the preparation of uncontaminated water, uncontaminated water can be obtained by continuous operation of the system. When the operation stops, however, airborne bacteria can invade the system thereby contaminating the same. Accordingly, it is important to prevent bacterial invasion and this is possible by the present system.

FIG. 3 shows an apparatus having an alcohol-pouring port (11) provided at the top of the housing (7) and an alcohol-discharging port (12) provided at the bottom of the housing (7). These ports allow the sterilization of the filtering material in the housing and the removal of materials which clog the filters. The housings are connected in series by the flow pipe 8 provided with valve 9. Accordingly, the present water-purifying system is very useful in practical operations. The system of the present invention can be used for preparing uncontaminated water and is useful for treating water having relatively massive contents of low molecular weight compounds. This system is periodically sterilized to ensure the purity of the system over long term periods. Thus, the water-purifying system which has alcohol inlet and outlet ports is a practical system. Also it is possible to remove clogging substances from the membrane by discharging alcohol which has been left in the housing for 2–3 minutes.

Figure 4:
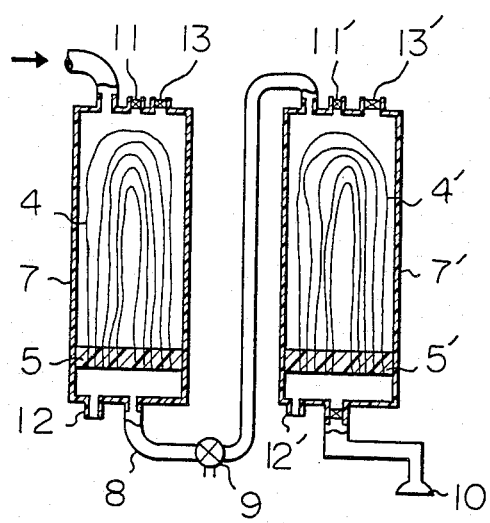
Figure 5:
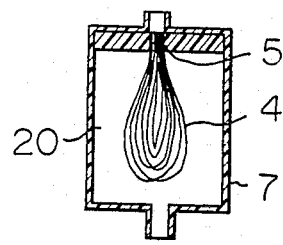
FIGS. 5 and 6 show examples of an automatic air venting system.
Figure 6:
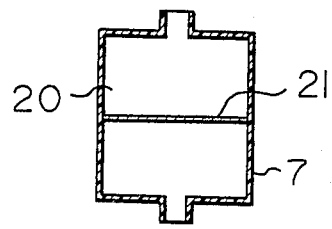

FIG. 4 shows another example of a multi-stage water-treating system in which air-vent (13) is provided for venting of air at the time alcohol is poured into the housing. For practical purposes it is important to install a mechanism to vent the air in the housing through the separating membrane which is permeable to air without permeating the water at a hydraulic pressure less than 5 kg/cm², as shown in FIG. 5 or FIG. 6. That is, contact-efficiency between the water to be treated and the filtering material is diminished and filtering efficiency is reduced by the presence of air in the housing. Usually, an air vent (13) equipped with a cock at the top of the housing is used, while in this invention, it is possible to mount an automatic air-venting device at the top of the housing. Also, it is possible to use a microporous flat membrane or hollow fiber made of a hydrophobic polymer such as polypropylene or polyethylene as the separating membrane permeable to air without being permeable to water under a hydraulic pressure of less than 5 kg/cm².

Having generally described this invention, a further understanding can be obtained by reference to certain specific examples which are provided herein for purposes of illustration only and are not intended to be limiting unless otherwise specified.

The microporous membranes used in the following examples have micro-structures as shown in FIG. 1 and with mean pore diameters and porosity being determined by the use of a Mercury Porosimeter device Model 221 manufactured by Calluro Elva Co., Ltd.

EXAMPLE 1

Porous hollow fibers made of polyethylene havin an internal diameters of 280μ, a wall thickness of 60μ, a porosity of 60 vol %, and a mean pore diameters 0.23μ were used. These hollow fibers were bundled into a U-shape as shown in FIG. 2, and the hollow open-ends were kept open and not occluded. The fibers were fixed by the use of polyurethane-resin at their tips and a filter of the cartridge type was obtained as a pyrogen-separating membrane. This separating membrane was mounted in the housing shown in FIG. 2, an was connected through a pressure-regulator to a well-water conduit. Water was passed through the device and filtered for 2400 hours at a back-pressure of 2.5 kg/cm², and pyrogen presence in the well water was measured before and after filtration. Non-filtered well-water shows a pyrogen content of ++. The results are shown in Table 1. The water permeability was 250 liters/m²/hr during the initial stage, and it was reduced to 170 liters/m²/hr after permeation for 480 hours. The separating membrane was once removed from the housing, and was washed with 50%-ethanol solution. The permeability recovered up to 210 liters/m²/hr, and after the further passage of water, the permeability was 160 liter/m²/hr after 2400 hours.

TABLE 1

| Water-passing time (hour) | 12 | 24 | 48 | 60 | 120 | 240 | 480 | 600 | 1200 | 2400 |
|---|---|---|---|---|---|---|---|---|---|---|
| Pyrogen | (−) | (−) | (−) | (−) | (−) | (−) | (−) | (−) | (−) | (−) |

As shown in Table 1, the present invention is effective for the removal of pyrogens from well-water.

EXAMPLE 2

As a separating membrane, a porous hollow fiber made of polypropylene having a pore diameters of 250μ at the hollow opening part, a wall thickness of 40μ, a porosity of 70 vol % and a mean pore diameters of 0.05μ was used. Other conditions were the same as those of Example 1 in which tap water was filtered, and pyrogens (if any) were measured in the tap water before and after filtration. The results are shown in Table 2. During the initial stage, the water permeability was 170 liters/m²/hr, which reduced to 125 liters/m²/hr after 480 hours of permeation. Similar to Example 1, the separating membrane was washed, and then the water permeability recovered up to 145 liters/m²/hr. Further filtration resulted in showing a water permeability of 120 liters/m²/hr after 2400 hours.

TABLE 2

| Permeation time (hour) | 12 | 24 | 48 | 60 | 120 | 240 | 480 | 600 | 1200 | 2400 |
|---|---|---|---|---|---|---|---|---|---|---|
| Pyrogen (if any) | (−) | (−) | (−) | (−) | (−) | (−) | (−) | (−) | (−) | (−) |

*(pyrogen ++ in non-filtered tap water)

As shown in Table 2, the present process is effective for the removal of pyrogens from tap water.

EXAMPLE 3

As a separating membrane, a porous hollow fiber made of polyethylene having an internal diameter of 250μ, a wall thickness of 40μ, a porosity of 80 vol %, and a mean pore diameter of 0.68μ was used. Other conditions were the same as those of Example 2 for filtering tap water. Pyrogen contents were measured on the tap water before and after filtration. The results are shown in Table 3.

TABLE 3

| Permeation time (hour) | 12 | 24 | 48 | 60 | 120 | 240 | 480 | 600 | 1200 | 2400 |
|---|---|---|---|---|---|---|---|---|---|---|
| Pyrogen (if any) | (−) | (−) | (−) | (−) | (−) | (±) | (±) | (±) | (±) | (±) |

*(pyrogen ++ in non-filtered tap water)

As shown in Table 3, during the initial stage of water-passage, pyrogen-removing efficacy was observed by the separating membrane which had a mean pore diameters ($\overline{D}$) which does not satisfy less than $0.002 \times (T) + 0.3$. However, the efficacy of filtration tended to reduce over long periods of water passage Thus, as in this invention, it was found that the desirable mean pore diameters (D) of the micropores should be less than $0.002 \times (T) + 0.3$.

The pyrogen-detecting method used in these examples was the Limulus lysate test (the limulus blood-cell dissolving gellation test). The detecting reagent used was Pregel (Trade name) manufactured by Teikoku Zoki Pharm. Co., Ltd. The detection is based on the principle that a pyrogen, even in a minor amount, reacts with the blood-cells in the blood lymph solution of limulus by which gelation occurs. The Pregel reagent is the above blood-cell ingredient frozen and dried and sealed tightly in an ampoule. In a test, a test solution was added to the ampoule, and after incubation for one hour at 37° C., it was kept for 5 minutes at room temperature, and the ampoule was slanted at 45-degrees in order to judge the degree of gelation. The judging criteria are as follows:

(++): Hard gel is formed, and the gel-shape does not collapse.

(+): Although a gel is formed, the mass moves by slanting the ampoule.

(±): Rough granular gel is formed and the viscosity is markedly increased.

(−): No change in the liquid as it is.

The detection limit of pyrogens by this method is $10^{-3}$ μg/ml.

EXAMPLE 4

As shown in FIG. 2, porous hollow fibers made of polyethylene having an inner diameter of 280μ, a wall thickness of 60μ, a porosity of 60 vol %, and a mean pore diameters of 0.25μ were bundled in U-shape, and the hollow-opening was kept in a non-occluded state. The bundle was fixed by polyurethane at the tip of the housing and the thus obtained adsorption-separating membrane material (3 m² of membrane surface area) was mounted in the housing. The housing was connected to a tap water conduit (O-City) through a pressure-regulator and an integrating flowmeter. After filtering 6,974 m³ of water at a back pressure of 1 kg/cm², the organic matter adsorbed in the adsorption-separating membrane was washed from the membrane with ethanol, and after evaporating ethanol, the weight was measured as 1.5455 g. The content of the organic matter in the tap water was 221.6 p.p.b. This organic substance was chemically analyzed in detailed by ordinary methods (quantitative and qulaitative analysis) including infra-red absorption spectrometry (IR), gap-chromatography (GC), and a gas-chromatography-mass analyzer (GC-MS). The results are presented in Table 4 which shows the various types of organic substances retained in minor quantities by the membrane.

TABLE 4

| Compound | Result of Analysis Content (p.p.t.) |
|---|---|
| Dibutyl phthalate | 290 |
| Dioctyl phthalate | 87 |
| Dioctyl adipate* | 5.5 |
| Diethyl phthalate | * |
| Dimethyl phthalate | * |
| Trichloro benzene | 24 |
| Dichloro benzene | * |
| Higher fatty-acids ester | ** |
| Higher fatty-acids | ** |
| Benzene | * |
| Toluene | * |
| Xylene | * |

Notes:
*Shows that the identification was possible, but quantification was impossible.
**Shows that detailed identification was not possible, and also, quantifiction was not possible.

EXAMPLE 5: (Model-test)

Distilled water containing 25.6 p.p.b. of dibutyl phthalate was prepared and this sample was used as test water. The same adsorption-separating membrane as shown in Example 4 was used for the filtration test. That is, 50 liters of the test water were filtered by the use of a pump at the rate of 3 liters/min, and the filtered water was analyzed for its dibutyl phthalate content quantitatively by the ordinary method. The results are shown in Table 5.

TABLE 5

| Sample | Dibutyl phthalate | Removing rate |
|---|---|---|
| Before filtration | 25.60 ppb | — |
| After filtration | 0.95 ppb | 96.3% |

As listed in Table 5, the rate of impurity removal was 96.3%. Thus, the system was very capable of removing dibutyl phthalate contaminant present in water in very small amounts.

EXAMPLE 6

As the adsorption-separating membrane, a porous hollow fiber made of polypropylene having an inner diameter of 250μ, a wall thickness of 40μ, a porosity of 70 vol %, and a mean pore diameters of 0.06μ was used. Under the same conditions as those of Example 5, filtration was tested, and the filtered water was analyzed quantitatively on dibutyl phthalate. The results are shown in Table 6.

TABLE 6

| Sample | Result of Analysis Dibutyl phthalate | Removing rate |
|---|---|---|
| Before filtration | 25.60 ppb | — |
| After filtration | 0.90 ppb | 96.5% |

As shown in Table 6, the removal rate was as high as that of the case of a polyethylene-porous hollow fiber (Table 5).

EXAMPLE 7

Under the same conditions as those of Example 5, a filtering test was performed by the use of a microporous polyethylene hollow fiber which was the same as that of Example 4, except that the mean pore diameter was 0.94μ. The content of dibutyl phthalate was measured in the filtering water, and the results are shown in Table 7.

TABLE 7

| Sample | Result of Analysis Dibutyl phthalate | Removing rate |
|---|---|---|
| Before filtration | 25.60 ppb | — |
| After filtration | 7.68 ppb | 70.0% |

The rate of removal was 70.0% as shown in Table 7, and the mean pore diameters of the micropores was a little large at 0.94μ. The rate of removal was slightly reduced in comparison to Example 5 or 6.

COMPARATIVE EXAMPLE 1

A filtration test was performed under the same conditions as those of Example 5 by the use of cellulose-type fiber having an inner diameter of 270μ, a porosity of 65 vol %, and a mean pore diameter of 0.30μ. The diphthalate content was measured in the water after filtration.

The results are shown in Table 8.

TABLE 8

| Sample | Dibutyl phthalate | Removing rate |
| --- | --- | --- |
| Before filtration | 25.60 ppb | — |
| After filtration | 24.55 ppb | 4.10% |

As shown in Table 8, the rate of removal was as low as 4.10% in the case of the cellulose-type, porous hollow fiber. These results confirm that a higher rate of removal of organic substances is a function of the polyolefin material of the present membranes.

EXAMPLE 8

As shown in FIG. 2, a U-shaped bundle was made from each porous hollow fiber (A) made of polyethylene having an inner diameters of $280\mu$, a wall thickness of $60\mu$, a porosity of 63 vol %, and a mean pore diameter of $0.35\mu$ and polyethylene-porous hollow fibers (B) having a pore diameters of $279\mu$, a wall thickness of $58\mu$, a porosity of 59.5 vol % and a mean pore diameter of $0.29\mu$. Keeping the hollow-open-ends open and the tip of the bundle fixed by polyurethane resin, the adsorption-separating membrane bundle (3 $m^2$ membrane surface area) was mounted in a housing made of polycarbonate. Two modular units, A and B were prepared. The two modular units were connected in series as shown in FIG. 3, and module-unit A was connected to a tap water conduit (N City), and a 2-stage filtration was performed at a back pressure 1.3 $kg/cm^2$. The filtered water showed the number of germs present as 0 pieces/ml and a negative (−) LAL-test. Thus, 98% of the low molecular weight organic substances in the original tap water was removed. The tap water originally contained 6 pieces/ml of germs and gave a positive LAL Test (++). In this case, the initial filtered flow rate was 3.8 liters/min., but the flow rate after passing 30,000 liters of water was 3.0 liters/min. Accordingly, the flow-reduction was minor.

COMPARATIVE EXAMPLE 2

In Example 8, modular-units A and B were each used separately, and when filtering at constant pressure at an initial filtering flow of 3.8 liters/min. each, the use of Module Unit (A) resulted in slowing the filtered flow at a rate as low as 3.0 liters/min. after the passage of 3,000 liters of water. With Module Unit B, the flow was reduced to 3.0 liters/min. after the passage of 2,600 liters of water.

EXAMPLE 9

A water passage test was performed similar to that of Example 8, except that the membrane surface area of Module Unit A was 4 $m^2$. The volume of water passed was 38,000 liters when the flow rate was reduced from 3.8 liters/min. to 3.0 liters/min.

EXAMPLE 10

A similar operation to that of Example 8 was conducted using a microporous polyethylene hollow fiber having a wall thickness of $56\mu$, a porosity of 66 vol %, and a mean pore diameters $0.45\mu$. A Module Unit (A) having a membrane surface area of 4.5 $m^2$ was manufactured. Similarly, by the use of microporous polyethylene hollow fiber having an inner diameter of $280\mu$ in the hollow-opening portion, a wall thickness of $60\mu$, a porosity of 63 vol %, and a mean pore diameter of $0.35\mu$, Module Unit (B) having a surface area of 4 $m^2$ was manufactured. Moreover, Module Unit (C) which had a membrane surface area of 3 $m^2$ was prepared by the use of microporous polyethylene hollow fibers having an inner diameter of $279\mu$, a wall thickness of $58\mu$, a porosity of 63 vol % and a mean of $0.29\mu$. Module-units (A), (B) and (C) were connected in series, and a water-passage test was performed similar to that of Example 1. As a result, the filtered water showed 0 germ/ml and a negative LAL test (−). The removal rate was 99.5% for the low molecular weight organic substances in the original water which initially contained 5 germs/ml and exhibited a positive LAL test (++). In this case, when filtering the water under a constant pressure at an initial filtering flow of 3.8 liters/min., the water-passing volume was 59,000 liters up to the time at which the flow rate reduced to 3.0 liters/min.

EXAMPLE 11

Module Units (A) and (C) in Example 10 were connected in series, and a water-passage test was performed similarly. The volume of water passed was 41,000 liters up to the time when the initial flow 3.8 liters/min. was reduced to 3.0 liters/min.

EXAMPLE 12

In Example 8, after passing 30,000 liters of water, the water in the housing of Module Unit (A) was discharged. Then, the module was filled with ethyl alcohol and was left to stand for about 30 minutes at room temperature. Next, ethyl alcohol was replaced by water, and after discharging water for about 10 minutes, the flow of water recovered up to 94% of the initial flow rate of water in a series connection of Module Units (A) and (B).

EXAMPLE 13

Figure 7:
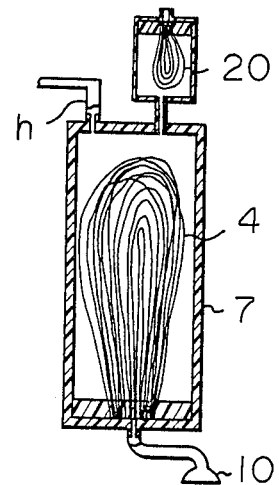

A water-treating apparatus composed of a housing and filtering material as shown in FIG. 7 was prepared. As a housing, a transparent cylinder of polycarbonate resin was used. The separating membrane was mounted (20) at the top of the housing as shown. This separating membrane unit was made from a microporous polyethylene hollow fiber having a mean pore diameters of $0.23\mu$, a wall thickness of $56\mu$, and an inner diameter of $280\mu$. The membrane was bundled and bent into a U-shape and attached with resin at its tip as shown in FIG. 5 within a cylinder-like plastic container. The surface area of the separating membrane was 0.02 $m^2$. Next, the water-treating system was mounted at a city water tap through a pressure gauge and a flow meter to measure the passage of water. The discharge of air inside the housing was observed. The discharge of air from the module was performed smoothly, and the water to be treated fully filled the housing. The water pressure at this point was 2.5 $kg/cm^2$ and the flow was 3.5 liters/min. Under the above conditions, while passing water continuously, the discharge of air present in the filtering material was observed. Air bubbles were observed for about 10 minutes, but a smooth discharge was made from the separating membrane, and no bubbles were found after about 10 minutes. It was confirmed that the air in the housing had discharged. No water leakage was observed. Next, by closing the tap of the city water to stop the operation after 24 hours, the inside of the housing was observed. Air was observed at the top of the housing. Again, by opening the tap of the city water, air was completely discharged after about 30 seconds. In this state, water was passed continuously for about 10 days, with no water leakage observed. Air did not stay in the housing. By the above waterfiltration test it was confirmed that the method of this invention permitted the ready venting of air during water treatment.

EXAMPLE 14

A flat membrane made of polypropylene (thickness of 0.3 mm, a mean pore diameters of $0.08\mu$) was fixed in a cylinder-like plastic container as shown in FIG. 6. This separating module was mounted at the top of the housing of the same water-filtering system as that in Example 13, and a water passage test was performed under the same conditions as those of Example 13. The results were the same as those of Example 13, and the air in the housing was smoothly discharged. No water leak was observed from the separating membrane. Thus, the efficacy of this invention was confirmed.

EXAMPLE 15

A module was prepared having a germ-removing filter formed from microporous polyethylene-hollow fibers. The hollow fiber had a mean pore diameters of $0.30\mu$, a porosity of 60 vol %, a wall thickness of $60\mu$, and an inner diameter of $280\mu$. The hollow opening part was bundled into a U-shape, and the tip of the bundle was fixed by a polyurethane resin to the housing as the bundle was mounted in the housing made of a polyvinyl chloride resin. Next, as shown in FIG. 7, an outlet for treated water was mounted onto the housing in order to prevent recontamination of water with bacteria. The outlet was a shower nozzle made of ABS and provided with about 2% of adsorbed iodine. Water warmed to 40° C. by a heater was sent to the hollow fiber module at a back pressure of 2 kg/cm² and was filtered. Table 9 shows the number of bacteria in water before and after filtration as well as the pyrogen content by the limulus test. Also, Table 9 shows the results obtained up to and including 3 months of water passage at 2 hours/day.

TABLE 2

|  | Initial stage of water-passing | After 1 month | After 2 months | After 3 months |
|---|---|---|---|---|
| Number of germs |  |  |  |  |
| Before filtration | 14 | 17 | 29 | 16 |
| After filtration | 0 | 0 | 0 | 0 |
| Pyrogen |  |  |  |  |
| Before filtration | (++) | (++) | (++) | (++) |
| After filtration | (−) | (−) | (−) | (−) |

As shown in Table 9, even though the system was not disinfected over the 3 month period, yet, germ free and pyrogen free water was continuously produced. The water discharged from the shower-nozzle was free of iodine odor and proved to be no problem for use as water for washing hands before surgery.

Having now fully described the invention, it will be apparent to one of ordinary skill in the art that many changes and modifications can be made thereto without departing from the spirit or scope of the invention as set forth herein.

What is claimed as new and is intended to be secured by Letters Patent is:

1. A multi-stage filtering system for the treatment of well water or tap water, consisting essentially of: means for enabling filtration of pyrogens and low molecular weight organics from water by the cooperative action of filtration and absorption, including:

a plurality of housings connected in series each provided with an inlet for water and an outleet for water so that water entering the first of said housings continously flows through the pluality of housings and exits the last of the housings and with a filtering membrane of a plurality of hollow, microporous polyolefin fibers each having openin opposite ends, each having a wall thickness (T) of $10-100\mu$, and each fiber having a multitude of rectangularly shaped nodule areas with each nodule area containing a plurality of strip-like microfibrils arranged in a longitudinal direction from one surface of a nodule to the side opposite said surface thereby forming a plurality of strip-like micropores having a mean pore diameter (D), which satisfies the relationship $0.03\mu < D \leq 0.002 \times T + 0.3\mu$, which form a micropacked structure, said plurality of fibers, each having a porosity measured by a mercury porosimeter of 20–90 vol. %, being bent in a U-shape such that all of the open ends of the fibers are collected and maintained in position at the inlet or outlet of each housing by being embedded in a resin plug, said embedding not precluding each fiber and remaining open, wherein the membrane in any given housing, which is defined as the $n^{th}$ stage of filtration, is defined by the relationships: $An \geq An+1$ and $Sn > Sn+1$, wheren An is the mean pore diameter of the membrane in the $n^{th}$ filtering stage and Sn is the membrane surface area of the membrane in the $n^{th}$ filtering stage;

a means for preventing the contamination of said filtering system by invading bacterial provided in the water outlet in the last of said housings in series; and air venting means provided on each of said housing which allows the venting of air from each housing through a separating membrane within the air venting means which is permeable to air but impermeable to water under a hydraulic pressure less than 5 kg/cm².

2. The method of claim 1, wherein said microporous polyolefin fibers are composed of polyethylene or polypropylene.

* * * * *